United States Patent

Sputtek et al.

[11] Patent Number: 5,935,848
[45] Date of Patent: Aug. 10, 1999

[54] DEEP-FREEZING CONTAINER

[76] Inventors: Andreas Sputtek, Soerser Weg 3d, 52070 Aachen; Bernd Mingers, Gietherstrasse 17b, 47877 Willich, both of Germany

[21] Appl. No.: 08/817,264

[22] PCT Filed: Oct. 14, 1995

[86] PCT No.: PCT/EP95/04048

§ 371 Date: Jun. 17, 1997

§ 102(e) Date: Jun. 17, 1997

[87] PCT Pub. No.: WO96/11663

PCT Pub. Date: Apr. 25, 1996

[30] Foreign Application Priority Data

Oct. 17, 1994 [DE] Germany .............................. 44 37 091

[51] Int. Cl.[6] .................................................. C12M 3/00
[52] U.S. Cl. ............................ 435/307.1; 62/64; 62/341; 62/903
[58] Field of Search ............................... 62/64, 336, 341, 62/903; 435/284.1, 307.1

[56] References Cited

U.S. PATENT DOCUMENTS

| | | | |
|---|---|---|---|
| 3,776,411 | 12/1973 | Luckadoo . | |
| 4,018,911 | 4/1977 | Lionetti et al. | 424/101 |
| 4,074,753 | 2/1978 | Schmittle et al. | 165/184 |
| 4,107,937 | 8/1978 | Chmiel | 62/64 |
| 4,288,897 | 9/1981 | Withers, Jr. | 29/157.4 |
| 4,371,034 | 2/1983 | Yamada et al. | 165/108 |
| 5,320,119 | 6/1994 | Griffiths | 134/95.1 |

FOREIGN PATENT DOCUMENTS 2219886 9/1974 France .

*Primary Examiner*—David A. Redding
*Attorney, Agent, or Firm*—Panitch Schwarze Jacobs & Nadel, P.C.

[57] ABSTRACT

A container that may be closed all around is useful for deepfreezing suspensions of living cellular materials kept in elastic bags. The container has two plane-parallel thin-walled metallic plates (14, 16) secured in swivellingly interconnected frame halves (20, 22). When the frame halves (20, 22) are superimposed, the plates (14, 16) secured therein are arranged with parallel faces at a slight defined distance from each other and form an intermediate cavity (12) in which the bag is placed. When the container is closed, the plates (14, 16) press the bag arranged inside (12) the container and flatten it until it has a small defined thickness. A microporous layer (30) that considerably increases heat transfer to the coolant that surrounds the container is secured to the outer side of plates (14, 16) by an adhesive layer. Furthermore, since the homogeneously flattened bag has a high surface/volume ratio and is pressed until it has no folds or bulges, the cellular material may be quickly and controllably cooled.

8 Claims, 3 Drawing Sheets

DEEP-FREEZING CONTAINER

BACKGROUND OF THE INVENTION

The present invention relates to a container which is suited for deep freezing suspensions of living cell material in elastic bags.

Deep freezing makes it possible to maintain living biological cells for practically unlimited time. Thus, for example, before interventions which cause great blood loss and which can be scheduled electively, blood is taken from the patient, processed, and subsequently frozen and stored. It is consequently possible to build up a sufficient deposit of the patient's own blood, so that the patient can be provided with his own blood during the operation and afterwards. An infection of the patient with viruses causing hepatitis and HIV, possibly contained in foreign donor blood and not detectable owing to the "diagnostic window," is thereby reliably prevented. Moreover, the deep freezing, generally referred to as cryopreservation, makes possible the preparation of "quarantine preparations" from foreign donor blood, the bridging of temporary bottle-necks, and the stocking of rare blood groups.

Usually, the whole blood preserves which are taken are separated by centrifugation into erythrocytes and blood plasma and are then transferred to bags not affected by low temperatures. These are subsequently deposited in metal containers, with which they are dipped into liquid nitrogen for cooling. In order that the living cells are not damaged or destroyed during freezing, a controlled and rapid cooling with a high rate of cooling is necessary with erythrocytes. The usual metal containers nevertheless have the disadvantage that they enable only a limited heat transfer to the cooling medium so that, with unavoidable geometric inhomogeneities of the bag contained in the container, uncontrolled cooling can occur at least in these partial areas.

BRIEF SUMMARY OF THE INVENTION

Against this background, it is the object of the present invention to make available a container for deep freezing of suspensions of living cell materials found in elastic bags, with which a rapid and controlled cooling of the cell material is possible.

This object is accomplished by a microporous layer fastened to the outside of the container by means of an adhesive layer.

The microporous layer on the outside of the container raises the heat transfer to the cooling medium and thereby greatly increases the rate of cooling, so that a rapid and controlled cooling of the cell material is possible, and the survival rate of the cell material deep frozen with the container of the invention is thereby clearly increased.

In accordance with a preferred further embodiment of the invention, the microporous layer comprises of textile materials. These can, for example, be constructed as a fabric tape of acetate rayon with a temperature-stable acrylate adhesive, so that the textile material can be simply and reliably fastened on the outside of the container and withstands repeated rapid cooling and reheating.

A particularly advantageous embodiment of the invention provides that the container has two thin-walled metallic plates arranged plane parallel, which form the container walls, and has a frame consisting of two halves, whereby appropriately the plates as well as the frame comprise material not affected by low temperature. Advantageously, one plate is respectively fastened in one frame half, the two frame halves are pivotably fastened to each other by at least one joint, and the plates fastened in the frame halves can be fixed in the plane parallel position by means of a fixing device. Advantageously, the plates fixed in the plane parallel position have at the same time a defined distance from each other, so that the bag placed in the container is pressed into a plate-shaped form with the required layer thickness upon closing the container. The container thereby presses the elastic bag into a basically homogenous plate shape, so that on the one hand, a large surface/volume ratio is attained, and on the other hand, geometric inhomogeneities such as folds or bulges are avoided. A further improved heat transmission is thereby attained, and an uncontrolled cooling due to inhomogeneities in shape is reliably prevented. Furthermore, the thin homogenous plate shape of the bag enables a space-saving storage and a rapid reheating.

Owing to this construction of the container in accordance with the invention, a simple and rapid handling is furthermore made possible, since the container for inserting and removing the elastic bag with the suspension can be completely opened up.

In a further embodiment, a seal is arranged in a frame half, which is advantageously constructed as a soft material seal and is stable at low temperatures, so that the interior of the container can be sealed fluid tight. This seal can be made of PTFE or another suitable material.

Since the elastic bags which receive the suspension usually have connection ports and pilot tubes, one or more recesses are advantageously arranged on at least one of the plates and are so constructed as to be able to accommodate connection ports or pilot tubes. In this way, these do not impede closing the container, and the defined plane parallel distance between the two plates is guaranteed, even when using an elastic bag with connection ports. These recesses are advantageously closeable with a fluid-tight closure element, so that the cooling medium cannot get into the interior of the container.

A further embodiment provides that the plates have a surface roughness of <1 μm on their side oriented toward the interior of the container, so that thermal contact between bag and plates is ensured during the entire cooling process.

BRIEF DESCRIPTION OF THE SEVERAL VIEWS OF THE DRAWING

The invention is discussed below in greater detail on the basis of the figures, wherein.

DETAILED DESCRIPTION OF THE INVENTION

Figure 1:
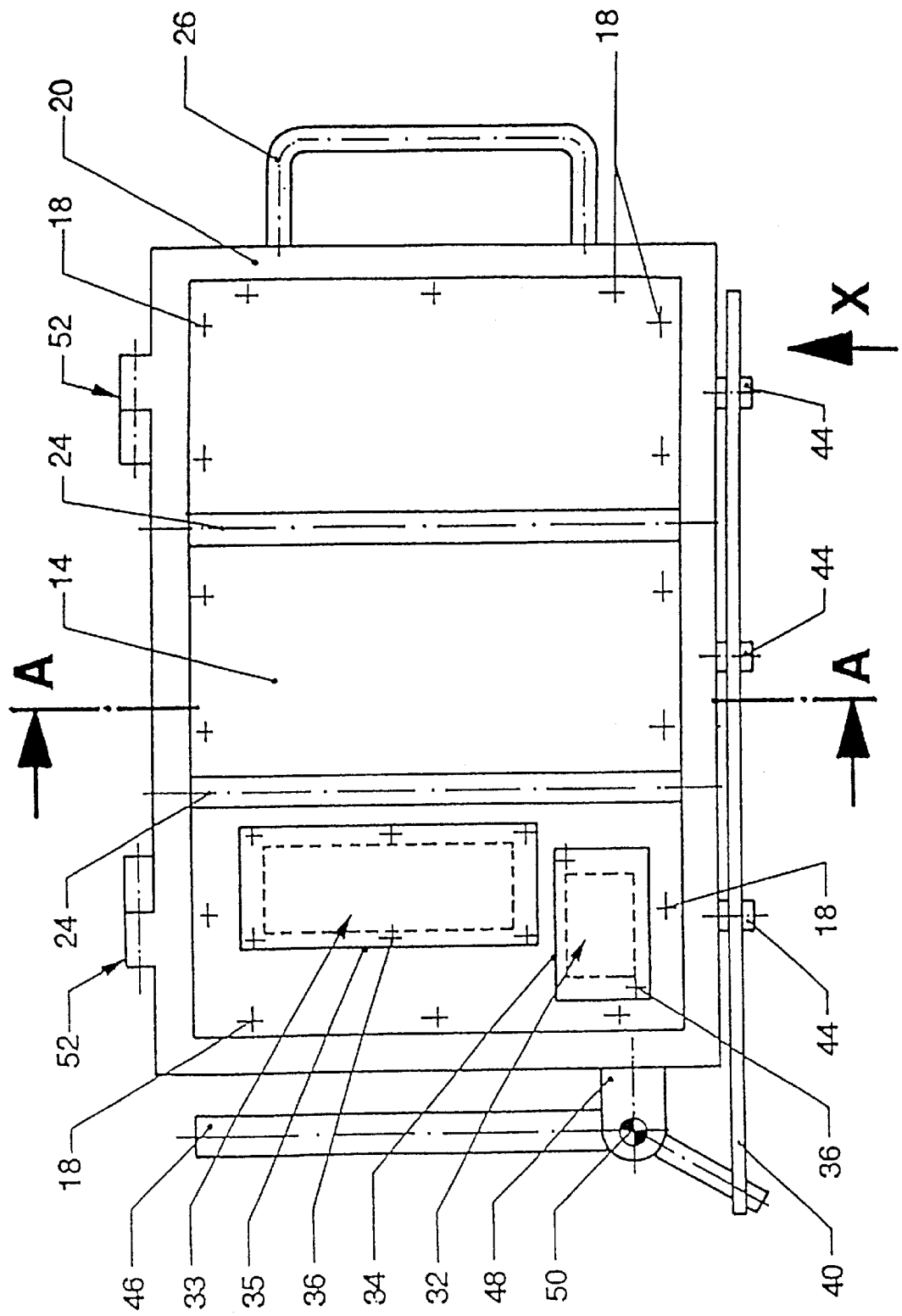
FIG. 1 shows a plan view of the container.

A plan view of the container is represented in FIG. 1. This basically comprises an upper plate and a lower plate, as well as a two-part frame, which comprises an upper frame half and a lower frame half. In this view, however, only the upper plate 14 as well as the upper frame half 20 is visible. This upper plate 14 is fastened with screws 18 to the upper frame half 20. This upper frame half 20 is pivotably connected by two hinges 52 with the lower frame half (not shown) and has two reinforcing elements 24 which in each case, in the embodiment here represented, consist of a round rod. These reinforcing elements 24 restrict to a defined degree the buckling of the plates 14, 16 which necessarily occurs upon freezing the suspension. Furthermore, a grip 26 is attached to the upper frame half 20, as well as holding lugs 44. These holding lugs 44 are engaged by a fixing device for locking the container together with the identical holding lugs 44 situated on the lower frame half. This fixing device comprises a lever 46 and a sliding block 40. The lever 46 of the fixing device is pivotable with a pin 50 mounted in a stand 48 fastened to the lower frame half. Finally, the upper plate 14 also has two recesses 32 and 33, which are provided respectively with a cover 34 or 35 constructed as a cap. The covers 34 and 35 are connected with the upper plate 14 by the screws 36. In this embodiment, the recess 32 accommodates a connection port (not shown), while the recess 33 accommodates pilot tubes for blood group determination, which are likewise not shown.

Figure 2:
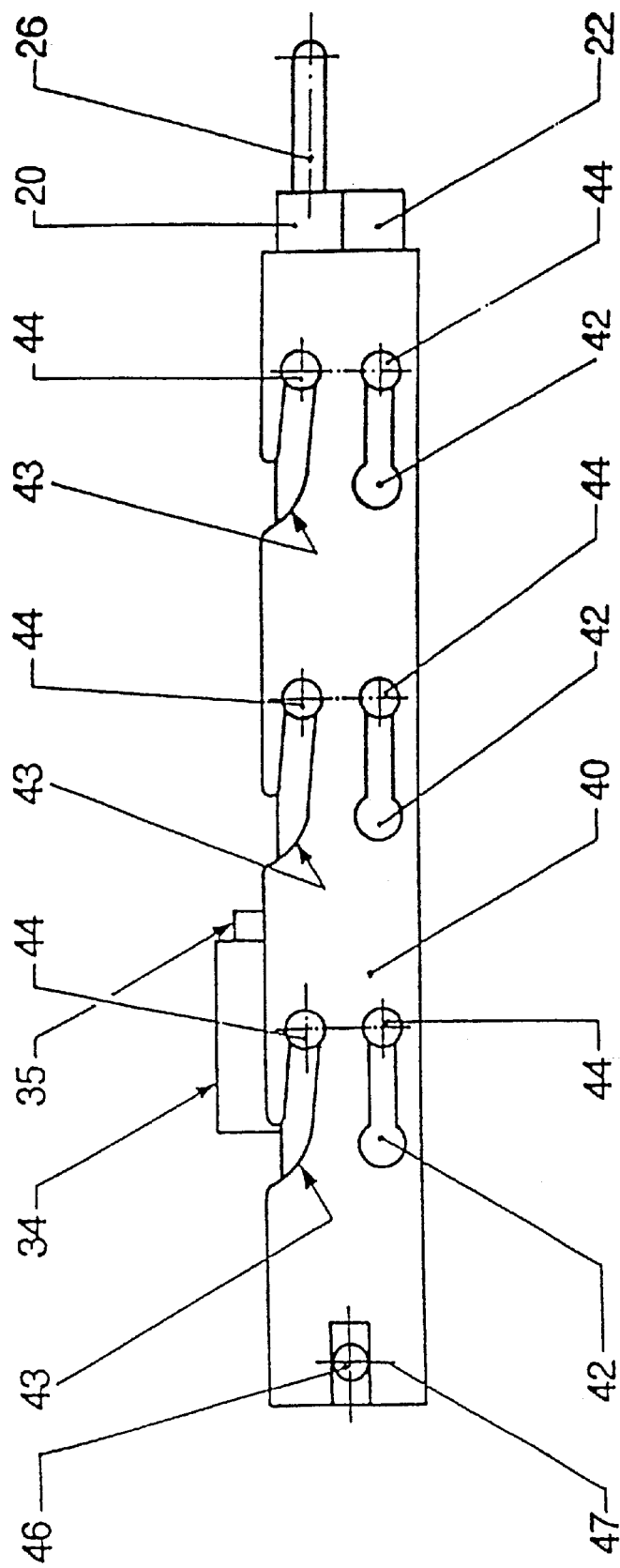
FIG. 2 shows a side view of the container in the direction of the arrow X in FIG. 1.

In FIG. 2, a side view of the container is represented in the direction of the arrow X in FIG. 1. As can be well recognized here, the sliding block 40 has a series of upper holding slots 42 (sic) and a series of lower holding slots 43 (sic). These holding slots engage the holding lugs 44 of the upper frame half 20 and the lower frame half 22 when these lie one upon the other. The lower holding slots 42 therein are closed on all sides, while the upper holding slots 43 are upwardly open. The sides of the holding slots 43 point up to their opening with a slight inclination. The lever 46 has a pivoting connection with the sliding block 40 by means of a pin indicated by the dash-dotted line 47. The grip 26 arranged on the upper frame half 20 can likewise be well recognized here, as well as the cover 34 constructed as a cap, which closes off the recess 32 arranged in the upper plate half 14.

Figure 3:
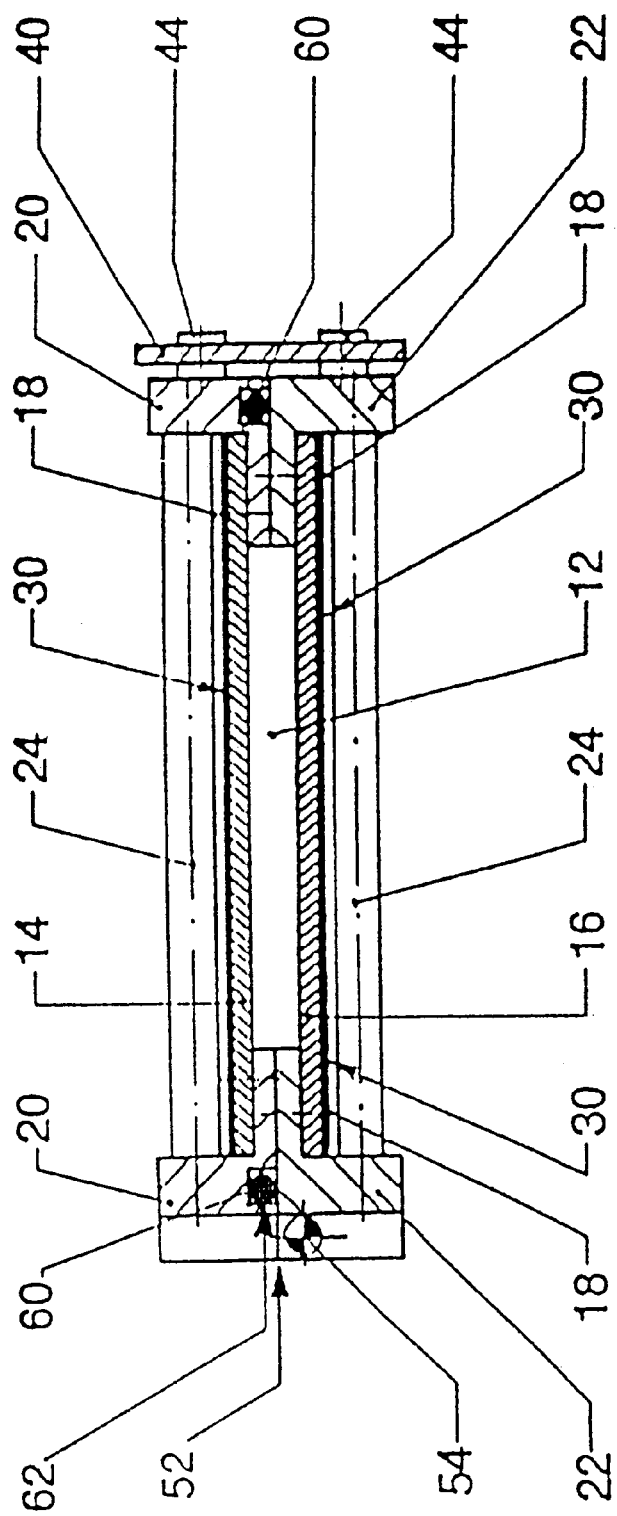
FIG. 3 shows a section through the container along the line A—A in FIG. 1.

A section through the container along the line A—A of FIG. 1 is represented in FIG. 3. The upper plate 14 and lower plate 16 forming the container walls are respectively connected with the upper frame half 20 or the lower frame half 22 by the screws indicated by lines 18. A microporous layer 30 is mounted respectively on the outside of the upper plate 14 as well as of the lower plate 15, and comprises a textile material in the example here represented, which is fastened with a low temperature-stable adhesive layer to the outside of the upper plate 14 and the lower plate 16. A groove 62 is worked into the upper frame half 20 in which a seal 60 is arranged. This is constructed as a low temperature-stable, soft material seal in the embodiment described, and seals fluid tight the container interior formed between the upper plate 14, the lower plate 16, the upper frame half 20 and the lower frame half 22. The upper frame half 20 and the lower frame half 22 have reinforcing elements 24 in each case and have a pivoting connection with each other through the pins 54 located in the hinges 52. The hinges 52 and the pins 54 are at the same time preferably constructed of materials with basically equal coefficients of expansion, so that a jamming is avoided and the mobility of the joints is guaranteed even at low temperatures. The holding lugs 44 arranged on the upper frame half 20 and the lower frame half 22 are engaged by the sliding block in the closed position of the container. The container is held in the closed position by self-locking between the inclined sides of holding slots 42 or 43 and the holding lugs 44.

The functioning of the container of the invention will be explained below with reference to FIGS. 1 to 3, described thoroughly above. The suspension destined for freezing living cell material is poured into an elastic bag suitable for deep freezing, and this bag is then laid in the container interior 12. For this, the upper frame half 20 is swung open upwardly, so that the container interior 12 is accessible. The bag is then laid in this, and the upper frame half 20 is then swung downward until it lies on the lower frame half 22. The upper plate 14 and the lower plate 16 are here respectively so fastened in the appropriate frame halves 20 or 22, that in the closed condition of the container they are arranged plane parallel with little distance from each other. Upon closing the container, the inserted bag is thereby pressed into a plate-shaped form with a small, defined layer thickness, whereby it almost completely fills the container interior 12 and lies on the inside of the upper plate 14 and on the inside of the lower plate 16. In this way, geometric inhomogeneities, such as folds or bulges, are avoided, so that the bag has a basically homogenous plate shape, and a large surface/volume ratio is thereby attained. In connection with the microporous layer 30 mounted on the outside of plates 14 and 16, which clearly increases the heat transfer to the cooling medium surrounding the container, a rapid and controlled cooling of the cell material is thereby possible, so that the survival rate of the deep frozen cell material is clearly increased with the container of the invention.

The reinforcing elements 24 arranged on the frame halves 20 and 22 restrict the buckling of plates 14 and 16 which necessarily occurs when freezing the suspension, so that the homogenous plate shape of the elastic bag located in the container is basically guaranteed.

After the bag is placed in the container interior 12 and the upper frame half 20 is swung onto the lower frame half, the upper frame half 20 and the lower frame half 22 are locked with each other by means of the siding block 40. The sliding block 40 is continuously joined with the lower frame half 22 by the holding slots 42 closed on all sides, on which, however, it can be slid back and forth owing to the slot-shaped construction of the holding slots 42. When the upper frame half 20 is swung onto the lower frame half 22, the holding lugs 44 arranged on the upper frame half 20 fit into the upwardly open upper holding slots 43 of the sliding block 40. By swinging the lever 46 mounted pivotably on the stand 48 with the pin 50, the lever 46 moves the sliding block 40 so that the upper and lower holding slots 43 or 42 constructed on the sliding block 40 enclose the holding lugs 44 arranged on the upper frame half 20 and the lower frame half 22. The inclined construction of the sides of the upper holding slot 43 leads to a strong tightening of the upper frame half 20, whose strength depends upon the path described by the lever 46 in closing. In this way, the upper frame half 20, and the lower frame half 22 are locked together so that the container interior 12 is closed on all sides. Self-locking between the sides of the holding slots 42 or 43 of the sliding block 40 and the holding lugs 44 brings about a force-locking fixation of the sliding block 40 and at the same time the lever 46, so that a spontaneous opening of the container or a slackening of the locking force is prevented. Through the seal 60 arranged in the upper frame half 20 in the groove 62 formed therein, the container interior 12 is moreover sealed fluid-tight, so that the cooling medium surrounding the container cannot get into the container interior 12.

The container thus securely closed can now be grasped by the grip 26 and dipped into liquid nitrogen for freezing of the cell material contained in the container.

We claim:

1. A closable container for deep freezing suspensions of living cell material, comprising an interior area for holding elastic bags containing suspensions of living cell material and a microporous layer fastened on the outside of the container by means of an adhesive layer, wherein said microporous layer comprises a textile material.

2. The container according to claim 1, characterized in that the container has two thin-walled metal plates arranged plane-parallel which form container walls, and a frame comprising two halves, wherein said walls and said frame define the interior area of said container.

3. The container according to claim 2, characterized in that respectively one plate is fastened in one frame half, and both frame halves are pivotably fastened to each other by means of at least one joint.

4. The container according to claim 2 characterized in that the plates fastened in the frame halves can be fixed in the plane parallel position using a fixing device.

5. The container according to claim 2 characterized in that the container interior can be sealed fluid-tight by a seal arranged in a frame half.

6. The container according to claim 2 characterized in that at least one of the plates has at least one recess for connection ports or pilot tubes arranged on the elastic bag.

7. The container according to claim 6, characterized in that the recess can be closed fluid-tight with a closure element.

8. The container according to claim 2 characterized in that the plates have a surface roughness of <1 $\mu$m on their side oriented toward the container interior.

* * * * *